United States Patent
Graham

(10) Patent No.: US 8,784,457 B2
(45) Date of Patent: Jul. 22, 2014

(54) IMPLANT FOR CORRECTING SKELETAL MECHANICS

(76) Inventor: Michael E Graham, Shelby Township, MI (US)

(*) Notice: Subject to any disclaimer, the term of this patent is extended or adjusted under 35 U.S.C. 154(b) by 676 days.

(21) Appl. No.: 12/904,780

(22) Filed: Oct. 14, 2010

(65) Prior Publication Data

US 2012/0095465 A1    Apr. 19, 2012

(51) Int. Cl.
*A61B 17/80* (2006.01)
(52) U.S. Cl.
CPC ........... *A61B 17/809* (2013.01); *A61B 17/8061* (2013.01)
USPC .................................................. 606/286
(58) Field of Classification Search
USPC ......... 606/280, 281, 283, 284, 286, 297, 298, 606/299; 623/18.11
See application file for complete search history.

(56) References Cited

U.S. PATENT DOCUMENTS 7,931,680 B2 * 4/2011 Myerson et al. .............. 606/281

* cited by examiner

*Primary Examiner* — Anu Ramana
(74) *Attorney, Agent, or Firm* — Kile Park Reed & Houtteman

(57) ABSTRACT

Deformities present on the end of a bone, for example the end of the metatarsal bone making up part of the metatarsocuneiform joint, can lead to deformities such as bunions. These deformities are treatable with an implant that comprises a plate with a wedge extending perpendicular from the plate. Following removal of cartilage from the joint, deformed portions at the end of the bone are removed and the wedge is inserted in the joint and held in place when the plate is attached to the bones flanking the joint. This effectively fuses the two bones together. The wedge can be shaped in various ways depending on the particular deformity present.

8 Claims, 5 Drawing Sheets

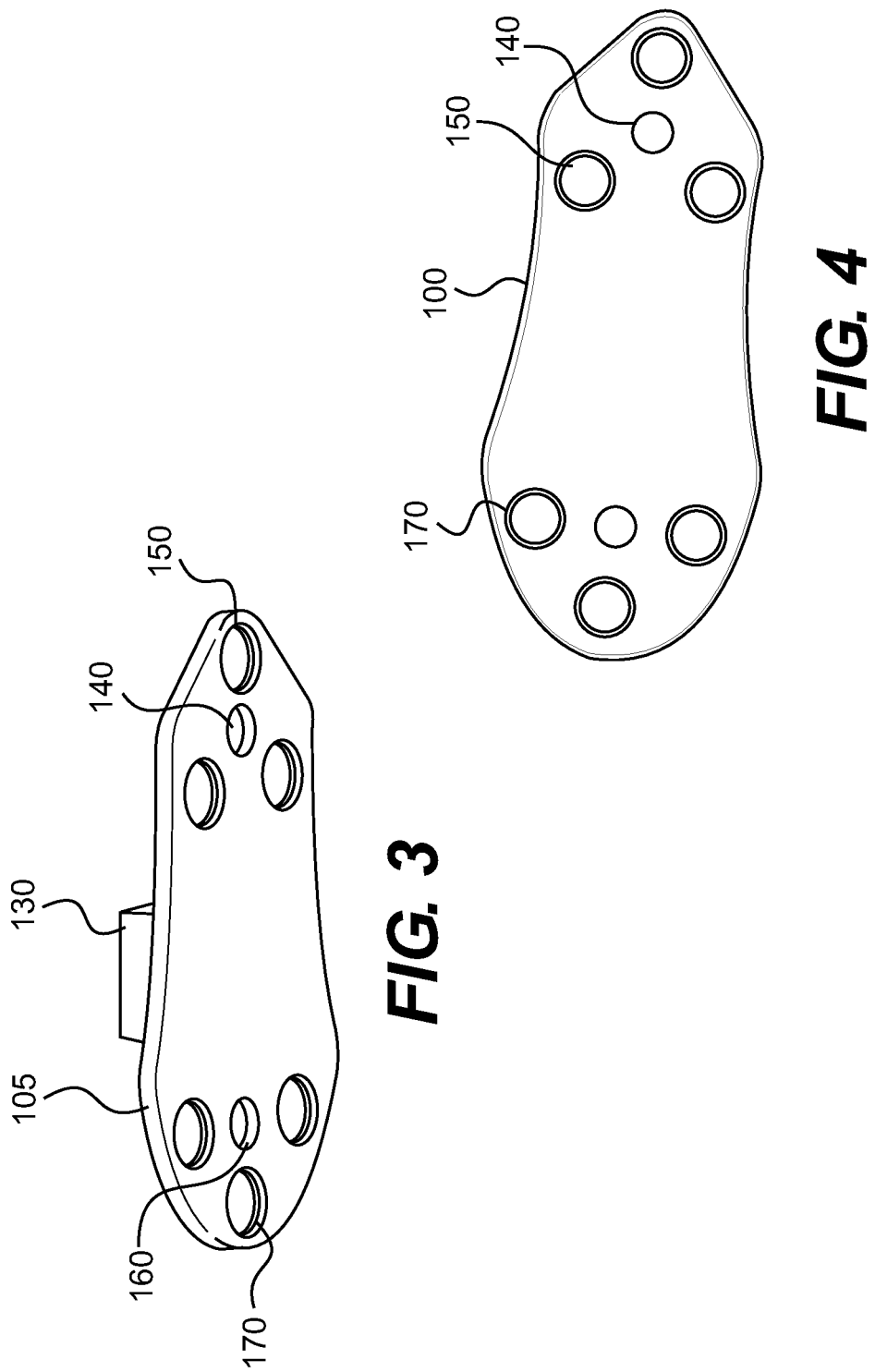

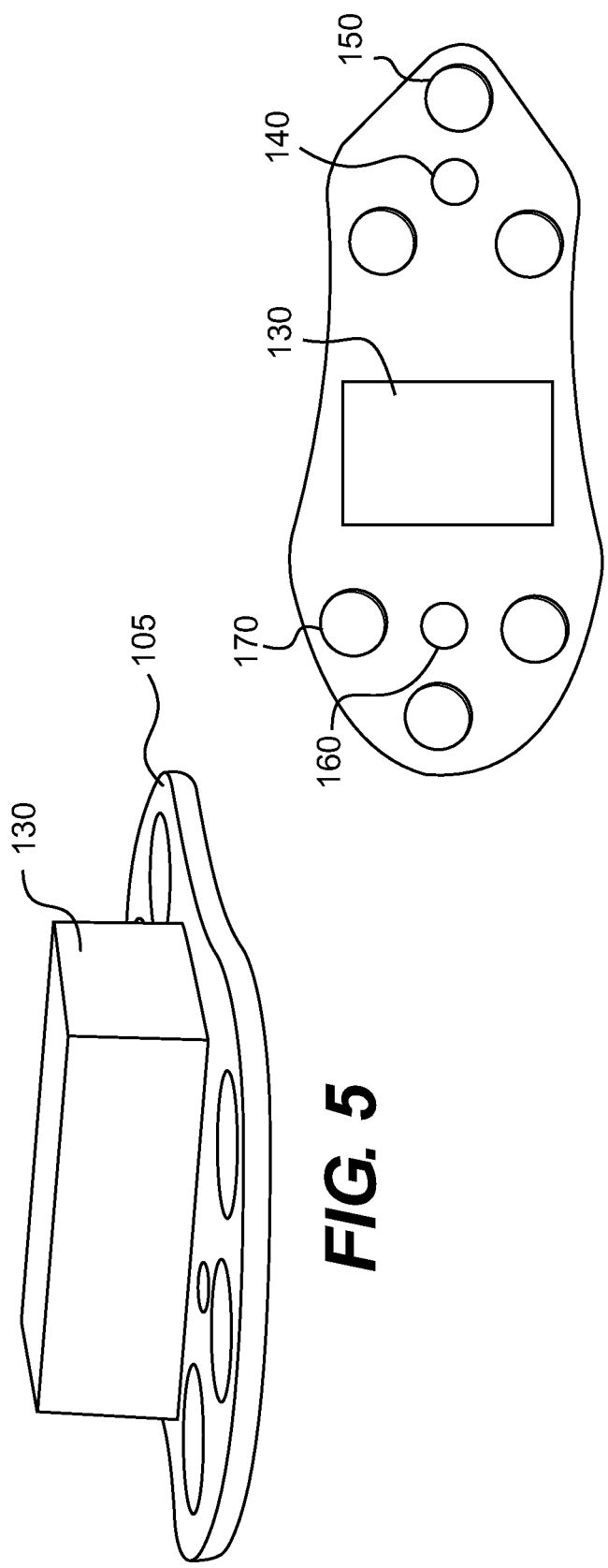

IMPLANT FOR CORRECTING SKELETAL MECHANICS

BACKGROUND OF THE INVENTION

This invention relates to a medical apparatus for enhancing and for correcting skeletal mechanics. More specifically, this invention relates to the correction of certain bone alignment deformities that impair optimal biped mechanics of the foot.

Excessive pronation (hyperpronation) of the foot leads to abnormal motion to the first metatarsal resulting in excessive strain on the soft tissues supporting this bone. After a prolonged period of these excessive forces the soft tissues will stretch out and no longer be able to support the first metatarsal. This instability leads to an abnormal deviation of the first metatarsal bone resulting in foot pathology. The deforming forces acting on the first metatarsal leads to three possible deviations: (1) pure medial deviation of the metatarsal, (2) dorsal deviation (dorsiflexion) of the metatarsal, and (3) the combination of the previous two, dorsomedial deviation. When the first metatarsal deviates medially (toward the body's middle/away from the little toe) the hallux (big toe) will deviate laterally (toward the little toe). When the first metatarsal deviates dorsally (up), the proximal phalanx of the hallux plantarflexes (angles down) and the distal phalanx angles dorsally. A dorsomedially deviated first metatarsal forces the hallux to deviate in a plantar-lateral direction.

In addition to the soft tissue laxity of the first metatarsocuneiform joint there exists another deforming force. Several tendons from the leg and foot attach to the hallux. When the muscles from these tendons contract to move the hallux, this will lead to a retrograde force on the first metatarsal. The generated force from this action will further contribute to the deviation of the first metatarsal bone. The end result is that there will be instability at both the proximal and distal joints of the first metatarsal bone. To reiterate, the problem is not with the metatarsal bone itself but with the joints at the ends of this bone.

Yet, another complicating factor in the formation of first metatarsal bone (or "first ray") deformities is the pathoanatomy of the end of the first or medial cuneiform bone. In a normal foot, the joint between the first metatarsal and first cuneiform should be straight across from medial to lateral. A common finding with first ray deformities is that the distal end of the cuneiform (the end in contact with the first metatarsal) is deformed. The end of a deformed cuneiform will commonly angle medially. In other words, the distal lateral portion of the cuneiform is longer than the distal medial portion of the bone. This deformation causes instability of the first metatarsal bone and contributes to the medial shift of the metatarsal bone.

The deviation of the first metatarsal bone leads to the formation of a bunion (hallux valgus) and can also lead to other deformities of the first ray. These other deformities include metatarsus primus elevatus, metatarsus primus varus, hallux abductovalgus, hallux limitus, hallux rigidus and metatarsus primus adductus. With all of these deformities, there is usually no actual intrinsic deformity of the first metatarsal bone itself. The deformities are proximal at the first metatarsal cuneiform joint or distal at the first metatarsophalangeal joint.

The current treatment of the deformity of the first ray ranges from conservative non-surgical to aggressive surgical procedures. Non-surgical treatment includes the use of an arch support, supportive shoes, taping and strapping, padding, etc. Multiple surgical procedures have been described for the realignment of the first metatarsal bone to the cuneiform and the proximal phalanx of the hallux. These osseous (or bone surgical) procedures include cutting and shifting of the first metatarsal bone into a more rectus (or straight) position and fusing the base of the first metatarsal bone to the first cuneiform.

The problem with non-surgical treatment options is that it is ineffective in eliminating the causative factor. Also, every step leads to further deformity of the metatarsal bone. Because the problem with this deformity is intrinsic, usually external remedies are ineffective in controlling the deforming forces.

Surgical remedies consist of various osseous procedures to realign the metatarsal bone to the hallux. These osseous procedures of the first metatarsal bone only provide for a cosmetic effect while the instability of the first metatarsal/first cuneiform joint (the metatarsocuneiform joint) still exists. These types of procedures straighten the metatarsal bone with respect to the hallux but leave instability at the first metatarsocuneiform joint. Since the instability at the first metatarsocuneiform joint still exists, the first metatarsal bone will eventually deviate again and lead to the occurrence of an overall foot deformity.

Another surgical procedure to correct this deformity of the first metatarsal bone has been suggested. The procedure involves, inserting either an opening wedge or a bone graft in the metatarsocuneiform joint. Still another method is to fuse the first metatarsal to the first cuneiform via arthrodesis (the fusion of two bones by surgical procedure or otherwise). These procedures lead to long recovery periods, at least six months, and can fail. Wedges can displace from the fusion site and bone grafts can fail at a rate of as much as 20-30%.

Another procedure is the shortening of the first metatarsal bone. Unfortunately, this transfers the body's weight to the head of the second metatarsal bone instead of the first. Often, further pathology ensues such as callus formation under the ball of the foot leading to further pain and possible ulceration. In normal ambulation, the weight of the body lands on the outer aspect of the heel and is transferred to and through the foot ending up through the first metatarsal bone. The second metatarsal head is not meant to take the weight of the body and it is possible for it to develop a stress fracture. This improper weight redistribution can lead to fractures in other parts of the foot.

A final set of procedures use plates of various shapes to stabilize the first metatarsal/first cuneiform joint while arthrodesis of these bones occurs. The problem with these procedures is that the plates mimic a screw or staple and stabilize the fusion site between the two bones. Consequently, there is still a shortening of the first metatarsal bone leading to the possibility of other ill effects. Moreover, these plates are rather bulky and usually have to be removed after bone arthrodesis is achieved.

BRIEF SUMMARY OF THE INVENTION

One of the primary purposes of the subject invention is to correct first ray deformities that arise to a significant extent from deformities at the metatarsocuneiform joint. This device will treat these deformities at their source. The inventor's device, a surgical implant, consists of a plate and a wedge. The plate is secured to both the metatarsal and cuneiform bones, preferably by bone screws. The wedge inserts, at least part-way, into the metatarsocuneiform joint, so as to contact at least a portion of the ends of the bones flanking this joint. A critical aspect of the invention is the removal of the tissue, including bone tissue, present in the metatarsocuneiform joint in a manner that allows restoration of the proper alignment of the first metatarsal bone relative to the first cuneiform bone. This typically involves removal of a pie shaped wedge of tissue within this joint and may also involve reshaping the ends of the bones. As described above, it is believed that a principal factor causing bone misalignment is deformities of the ends of bones.

BRIEF DESCRIPTION OF THE FIGURES

FIGS. 3-7 are perspective, plan, and side views illustrating the device from several different angles;

DETAILED DESCRIPTION OF PREFERRED EMBODIMENTS

Figure 1:
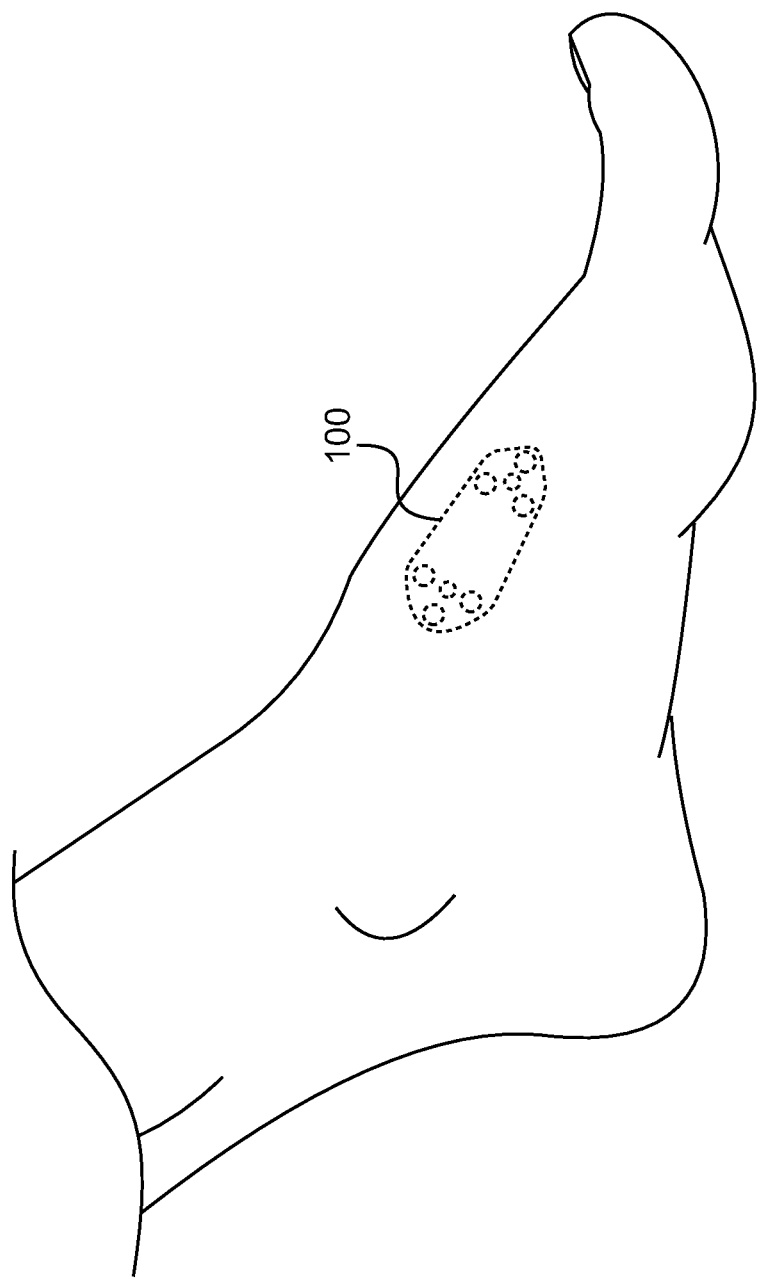
FIG. 1 illustrates an operative context of the invention where the device is implanted onto a patient's foot.

FIG. 1 illustrates a preferred location in which the subject implant for correcting skeletal mechanics 100 will be inserted. The implant 100 is placed at the inner, or medial, surface of a patient's foot over the metatarsocuneiform joint.

Figure 2:
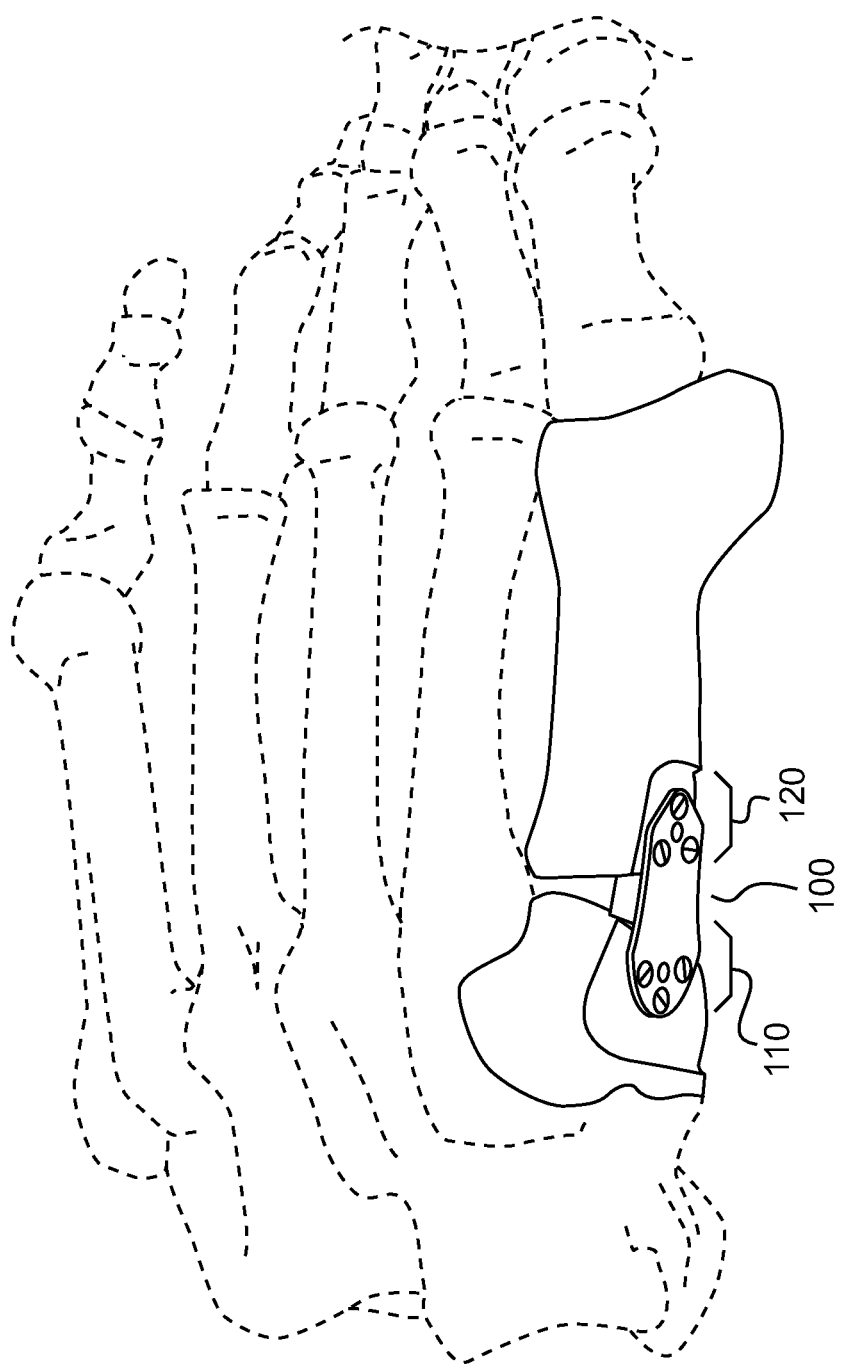
FIG. 2 illustrates the implanted device with the patient's bone structure exposed.

The device contains both a plate component 105 and a wedge component 130. See FIGS. 2-7 below. Turning to FIG. 2, the device is shown in place with the surrounding bone structure illustrated. The device is located such that the anterior portion of the plate is attached to a flush or flattened region on the side of the first metatarsal bone 120. The posterior portion is attached to a flush or flattened region on the side of the cuneiform bone 110. The wedge portion is inserted at least part way into the joint between these bones, the metatarsocuneiform joint.

FIGS. 3-7 show different detail views of a preferred implant. As stated above, the implant 100 is constructed with a plate component 105 and a wedge component 130. The wedge component 130 is attached to one side of the plate component 130. Also shown are small holes 140, 160 into which temporary pins are inserted as a preferable mechanism for temporary stabilization of the device. The pins are used to stabilize the plate during testing and to hold the device in place while the device is being permanently attached. The device is permanently attached, preferably, with bone screws. Shown surrounding the alignment pin holes 140, 160 are three anterior holes 150 and three posterior holes 170 through which bone screws are inserted to permanently anchor the plate to the underlying bone.

Small Length Wedge Design.

The inventor conceives of two distinct wedge designs, (1) a small wedge design which inserts into only the immediate sub-surface portion of the first metatarsocuneiform joint and (2) a large wedge design which extends the entire width of the first metatarsocuneiform joint.

One basic shape should be sufficient to treat many different types of metatarsal deviations. Also, if removal if the implant is desired, the small wedge design can be readily removed from the patient's foot without having to first break the implant into component parts. The small wedge design can extend to any distance into the metatarsocuneiform joint and still be fully functional. At the short end of the spectrum, the wedge need be no longer than necessary to make contact with, and secure in place, the ends of the bones flanking the joint. A preferred length of the wedge is from about 1 mm to about 20 mm.

Greater lengths would be desirable in certain circumstances, for example, if needed to fill a larger metatarsal deficit. This need could arise, for example, from a patient having a severe non-union from a previous surgery that left a very short first metatarsal. In addition to the use of longer wedge lengths, bone graft(s) could also be placed along with the device if necessary.

Large Length Wedge Design.

Figure 8B:
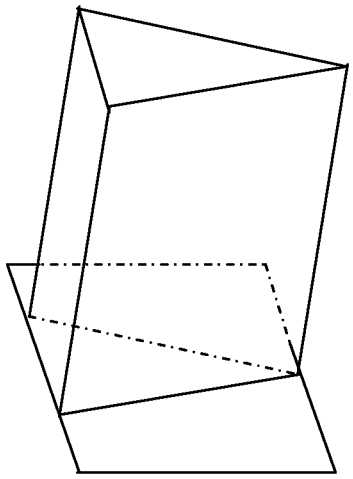
FIGS. 8A-8C illustrate the various shapes contemplated when large length wedges are used.
Figure 8C:
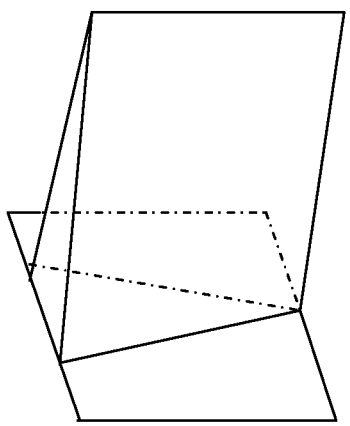
Figure 8A:
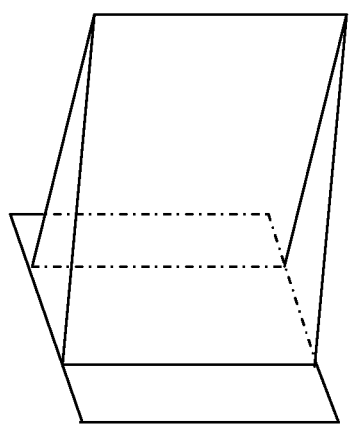

A large length wedge, illustrated in FIGS. 8A-8C, consists of various shapes designed to realign the first metatarsal back into normal alignment when the wedge is interpositioned into the joint. The length of the wedge has fenestrations that will allow bone to incorporate into the wedge to facilitate a fusion between the first metatarsocuneiform joint. The wedge will have a uniform taper with the widest part located at the base where it attaches to the plate extending to the tip the narrowest part.

As discussed previously, there are three common types of bone structure defects that lead to three deviations of the first metatarsal bone, (1) medial, (2) dorsal, and (3) dorsomedial. Taking this into consideration, three different variations of the wedge are presented. FIGS. 8A, 8B and 8C show preferred embodiments corresponding to each variation, respectively.

For the purely medially deviated joint, the wedge will be tapered uniformly from medial to lateral and dorsal to plantar on all sides. FIG. 8A. For the dorsally deviated first metatarsal, the proximal part of the wedge will be flat against the first cuneiform, it will not be tapered. This distal part of the wedge will be angled with the wider part being on the dorsal aspect of the wedge and taper to the narrower part of the wedge being plantar. FIG. 8B. A final design for the dorsomedially deviated first metatarsal consists of a wedge where the proximal end against the first cuneiform is not tapered from dorsal to plantar but the distal end against the first metatarsal is tapered. The narrowest part of the wedge is plantar and the wider part is dorsal and the overall attachment of the wedge to the plate is wider medially and tapers laterally. FIG. 8C.

Each of the three designed wedges will have incremental tapers to adjust for the severity of the deviation of the metatarsal. Trial wedges will be available, as part of the instrument set to determine the exact wedge shape needed for correction of a deformity. Due to the design of the wedges they will be marked as right or left foot and what plane of deviation(s) is corrected.

For any of the above described devices, a preferred design is to use bone screws to attach the plate to the first metatarsal and first cuneiform. The bone screws are preferably self-tapping. The threaded head of the screw enters the plate so that it is flush. This is because the part of the foot where the plate is to be placed is not covered with a lot of soft tissues and so a low profile is preferred.

The anterior upper edge device should be convexly curved so that the device does not extend above the upper surface of the bone to which it is attached. The preferred material of the plate and wedge is titanium, however, other potential materials could also be used or combination of materials including ceramic, various bone graft compositions, polymers and the like.

Insertion Procedure.

A preferred insertion procedure includes the steps of, after a foot and ankle are prepped and draped in the usual fashion, a 4-cm linear incision is made over the metatarsocuneiform joint. The soft tissue is dissected bluntly off these bones revealing the joint. The medial osseous prominence of the first cuneiform 110 is osteotomized to create a flush or flattened surface. A similar procedure is performed on the first metatarsal. 120. The lateral soft tissues of the joint are left intact.

The articular cartilage of the metatarsocuneiform joint is resected. One preferred method of cartilage removal is as follows. At the base of the first metatarsal a sagittal saw is used to remove the articular cartilage and also create a flush surface. At the distal aspect of the first cuneiform a sagittal saw is used to remove the articular cartilage present there. The goal is to remove as small amount of tissue as possible but enough so that there is osseous integration into the wedge.

With respect to the large wedge design, choosing the correct size wedge is important but will, most likely, not be possible before the operation. This is because the proper size will depend upon, not only the unique characteristics of the patient's deformity, but also the surgeons decision about how much tissue and bone to remove in any preceding preparatory steps.

Accordingly, the correct size wedge will be determined after the preceding preparatory steps with the aid of "trial sizers." The various trial sizers are placed in between these two bones to determine which sized wedge will be needed to achieve the desired correction. The correction achieved with a specific trial wedge can be visualized under fluoroscopy or radiological intra-operative study. There can be a separate set of trial sizers designed for each of the three main classes of deviations mentions above: medial, dorsal and dorsomedial.

Once the desired wedge size is determined it is placed into the joint space. Temporary pins are inserted into the bones to stabilize the plate while the more perminant screws are inserted into the bones. A stabilizing wire will then hold the end of the plate to the first metatarsal. Next, proximal screws are inserted into the cuneiform followed by screws placed into the first metatarsal. The temporary pins are then removed. The metatarsocuneiform joint is placed through a range of motion to visualize stabilization of the plate. Finally, radiographs or fluoroscopy are used to confirm the position of the screws and plate and the achieved correction. Being completely satisfied with the results of the placement of the bone plate and wedge soft tissues and skin are closed per surgeon's choice. A dry sterile bandage is placed on the foot and the patient is allowed to ambulate with a surgical shoe.

The subject implant facilely enables stabilization of the first metatarsal bone with the first cuneiform that corrects the deviation of the first metatarsocuneiform joint while preventing the shortening of the first ray. Also, prior art arthrodesis procedures required a long recovery period, often about six weeks, before weight could be bone by the fused bones. In certain embodiments of the disclosed invention weight can be born after only 3 to 5 days. This is because unlike prior art procedures in which the area of bone fusion must heal before it can bear weight, the combination of the plate and wedge provide the structural support.

The device is not limited to the embodiments disclosed above. Other embodiments include any plate with an attached blade/wedge that has unique shape that can been used on the small bones of the hand, foot, wrist, ankle etc. Further, that there are several versions of the wedge, including one that corrects in the transverse plane, one that corrects in the sagittal plane, and one with the combination of both transverse and sagittal planes. Additionally, there are various degrees of correction achieved of each of the wedges depending on the thickness of the wedge.

What is claimed is:

1. An implant, useful for treating bone abnormalities at a patient's first metatarsocuneiform joint, comprising:
    a plate component and a wedge component,
    said wedge component connected to and extending perpendicular from the plane formed by said plate component surface and dividing said plate component into an anterior portion and a posterior portion,
    and said wedge component being configured to insert into a patient's metatarsocuneiform joint,
    said anterior portion comprising three holes through which bone screws can be used to secure said anterior portion to a patient's first metatarsal bone,
    said posterior portion comprising three holes through which bone screws can be used to secure said posterior portion to the patient's cuneiform,
    said anterior portion has a flare having a first width, said plate component middle portion has a second width and said posterior portion has a flare having a third width,
    said third width is greater than each of the first and second widths, respectively,
    said second width is smaller than each of the first and third widths, respectively, and,
    wherein said implant treats bone abnormalities by inhibiting abnormal deviation of the first metatarsal bone.

2. An implant as defined in claim 1, further comprising:
    an anterior upper edge of said plate component is curved so that the edge does not extend above the patient's first metatarsal bone.

3. An implant as defined in claim 1,
    wherein temporary securing structures are present on said anterior portion and posterior portion to temporarily secure the implant in place.

4. An implant as defined in claim 1,
    wherein said wedge component extends out so that it covers the entire width of the patient's metatarsocuneiform joint.

5. An implant as defined in claim 1,
    wherein said wedge component extends out from the plate component a length in the range from about 1 mm to about 20 mm.

6. An implant for treating bone abnormalities in a patient's foot, said implant comprising:
    a base plate operable to be secured between opposing ends of a patient's metatarsocuneiform joint;
    a base plate anterior portion has a flare having a first width, a base plate middle portion has a second width and a base plate posterior portion has a flare having a third width,
    said third width is greater than each of the first and second widths, respectively,
    said second width is smaller than each of the first and third widths, respectively,
    said base plate having three having three apertures at each end for receiving bone screws to operably attach the base plate to a patients foot and
    a solid wedge component having a base portion connected to said base plate, said wedge component extending perpendicular from the plane formed by said base plate surface and being operable to project into a gap in a patient's metatarsocuneiform joint.

7. A method of treatment of bone abnormalities by fusing two bones comprising:
    an implant comprising:
        a plate component and a wedge component,
        said wedge component connected to and extending perpendicular out from the plane formed by said plate component surface and dividing said plate component into an anterior and a posterior portion,
        said wedge component being configured to insert into a patient's metatarsocuneiform joint, said anterior portion comprising securing structures to secure said anterior portion to the patient's first metatarsal bone, said posterior portion comprising securing structures to secure said posterior portion to the patient's cuneiform, wherein said method of treatment comprises the steps:

an incision is made and soft tissues are opened using standard procedures of the surgeon's choice to expose the metatarsocuneiform joint, a generally flush surface is created on the medial side of the first cuneiform bone, a generally flush surface is created on the medial side of the first metatarsal bone, a portion of the tissues present in the metatarsocuneiform joint are removed, said portion removed being sufficient to promote of proper alignment of the first metatarsal bone relative to the first cuneiform bone and sufficient to allow insertion of the wedge component into the metatarsocuneiform joint, the implant is temporarily secured to the flush surface of the metatarsal bone, after proper alignment is achieved the implant is permanently secured to the first metatarsal bone and the first cuneiform bone, the soft tissues and the skin are closed using standard procedures of the surgeon's choice.

8. A method of treatment of bone abnormalities as defined in claim 7 further comprising:

the implant is temporarily secured to the flush surfaces of the cuneiform bone and the metatarsal bone and the implant is tested to confirm the proper bone alignment is achieved.

* * * * *